US006325976B1

(12) United States Patent
Small et al.

(10) Patent No.: US 6,325,976 B1
(45) Date of Patent: Dec. 4, 2001

(54) CONTINUOUS ELECTROLYTICALLY REGENERATED PACKED BED SUPPRESSOR FOR ION CHROMATOGRAPHY

(75) Inventors: Hamish Small, Leland, MI (US); Yan Liu, Santa Clara, CA (US); John M. Riviello, Santa Cruz, CA (US); Nebojsa Avdalovic, Cupertino, CA (US); Kannan Srinivasan, Sunnyvale, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 09/031,221

(22) Filed: Feb. 26, 1998

(51) Int. Cl.[7] ................................................ G01N 30/02
(52) U.S. Cl. .......................... 422/70; 204/536; 204/542; 210/198.2; 436/161
(58) Field of Search ............................... 436/161; 422/70, 422/99; 210/635, 638, 656, 659, 662, 663, 198.2; 204/450, 520, 536, 542

(56) References Cited

U.S. PATENT DOCUMENTS

| 3,897,213 | 7/1975 | Stevens et al. . |
|---|---|---|
| 3,920,397 | 11/1975 | Small et al. . |
| 3,925,019 | 12/1975 | Small et al. . |

(List continued on next page.)

FOREIGN PATENT DOCUMENTS

| 0 555 962 A2 | 9/1993 | (EP) . |
|---|---|---|
| WO 96/27790 | 9/1996 | (WO) . |
| WO 96/27793 | 9/1998 | (WO) . |
| WO 99/11351 | 3/1999 | (WO) . |

OTHER PUBLICATIONS

Rabin et al., "New Membrane–Based Electrolytic Suppressor Device for Suppressed Conductivity Detection in Ion Chromatography" *J.of Chromatog*, 640:97–109 (1993).

(List continued on next page.)

*Primary Examiner*—Jan Ludlow
(74) *Attorney, Agent, or Firm*—Flehr Hohbach Test Albritton & Herbert LLP; David J. Brezner

(57) ABSTRACT

An electrolyitic suppressor including (a) a suppressor bed of ion exchange resin, (b) an electrode chamber adjacent the suppressor, (c) a first electrode in the electrode chamber, (d) a barrier separating the suppressor bed from the first electrode chamber preventing significant liquid flow but permitting transport of ions only of the same charge as the suppressor bed resin, (e) a second electrode in electrical communication with the resin bed, and (f) a recycle conduit between the suppressor outlet port and said electrode chamber. The second electrode may be in contact with the ion exchange resin in the suppressor or located in second electrode chamber. For anion analysis, the method of using the apparatus includes: (a) flowing an aqueous liquid sample stream containing anions to be detected and cation hydroxide through the separator bed, (b) flowing the aqueous effluent from the separator bed through the flow-through suppressor, (c) flowing the effluent liquid from the suppressor past a detector, (d) recycling said liquid effluent from the detector through a cathode chamber proximate to the suppressor bed and separated by the first barrier, and (e) applying an electrical potential between the cathode and the anode. Water is electrolyzed at the anode to cause cations on the cation exchange resin to electromigrate toward the barrier and to be transported across the barrier toward the cathode while water in the cathode chamber is electrolyzed to generate hydroxide ions which combine with the transported cations to form cation hydroxide in the cathode chamber.

10 Claims, 3 Drawing Sheets

U.S. PATENT DOCUMENTS

| | | |
|---|---|---|
| 3,926,559 | 12/1975 | Stevens . |
| 4,314,823 | 2/1982 | Rich, Jr. et al. . |
| 4,459,357 | 7/1984 | Jansen et al. . |
| 4,474,664 | 10/1984 | Stevens et al. . |
| 4,999,098 | 3/1991 | Pohl et al. . |
| 5,248,426 | 9/1993 | Stillian et al. . |
| 5,352,360 | 10/1994 | Stillian et al. ............... 210/198.2 |
| 5,567,307 | 10/1996 | Karmarkar . |
| 5,569,365 * | 10/1996 | Rabin et al. . |
| 5,597,734 | 1/1997 | Small et al. . |
| 5,633,171 | 5/1997 | Small et al. . |
| 5,759,405 | 6/1998 | Anderson, Jr. et al. ............. 210/656 |
| 6,027,643 * | 2/2000 | Small et al. . |

OTHER PUBLICATIONS

Petro et al., "Molded Monolithic Rod of Macroporous Poly(styrene–co–divinybenzene) as a Separation Medium for HPLC of Synthetic Polymers: "On–Column" Precipitation –Redissolution Chromatography as an Alternative to Size Exclusion Chromatography of Styrene Oligomers an dPolymers" *Analytical Chemistry*, 68(2):315–321 (Jan. 15, 1996).

* cited by examiner

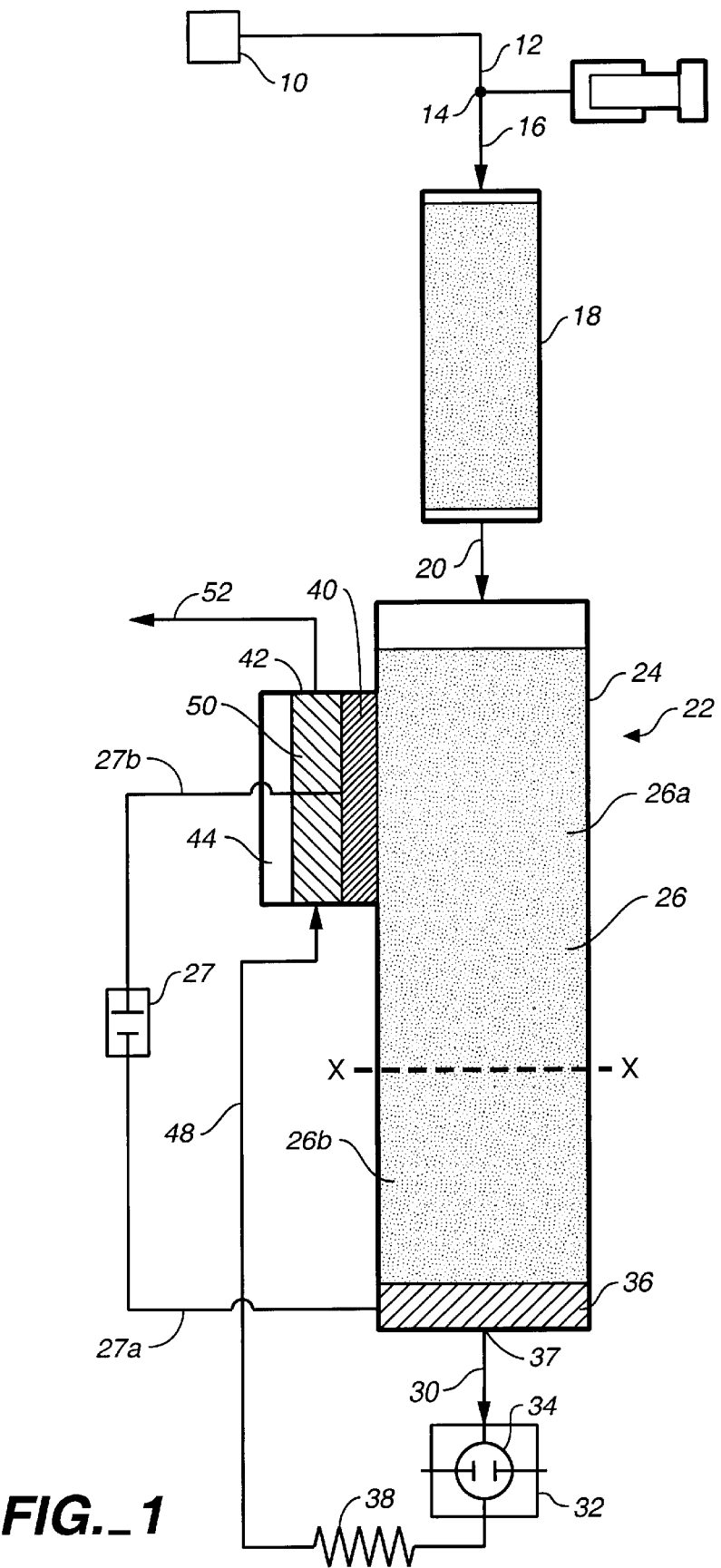
FIG._1

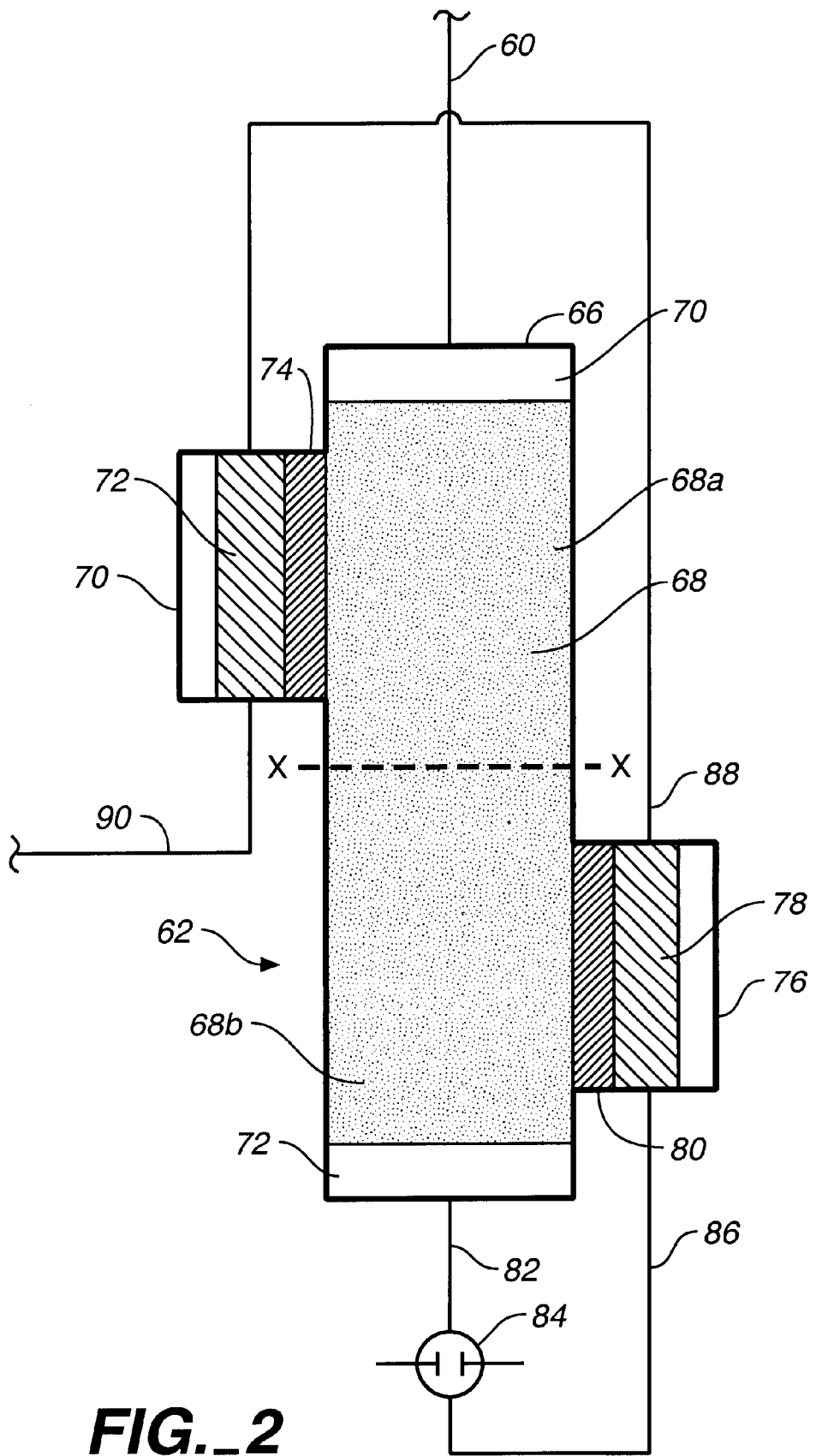
FIG._2

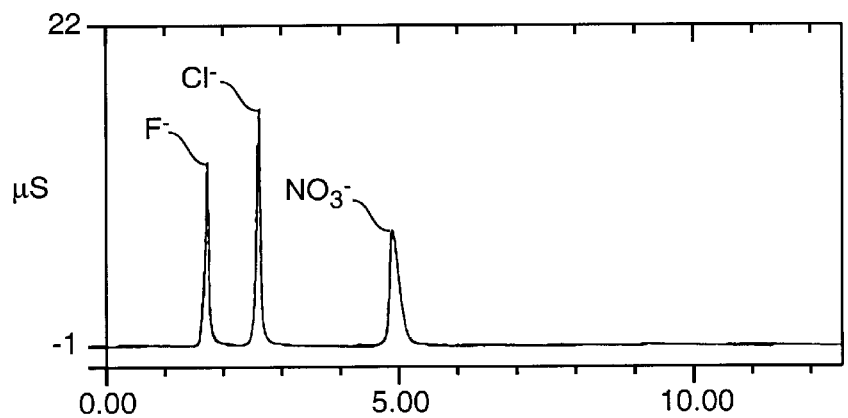
FIG._3
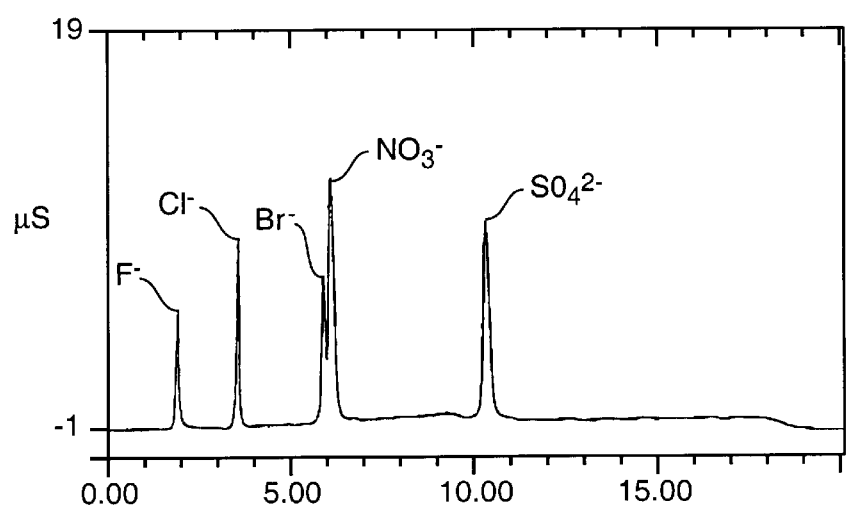
FIG._4
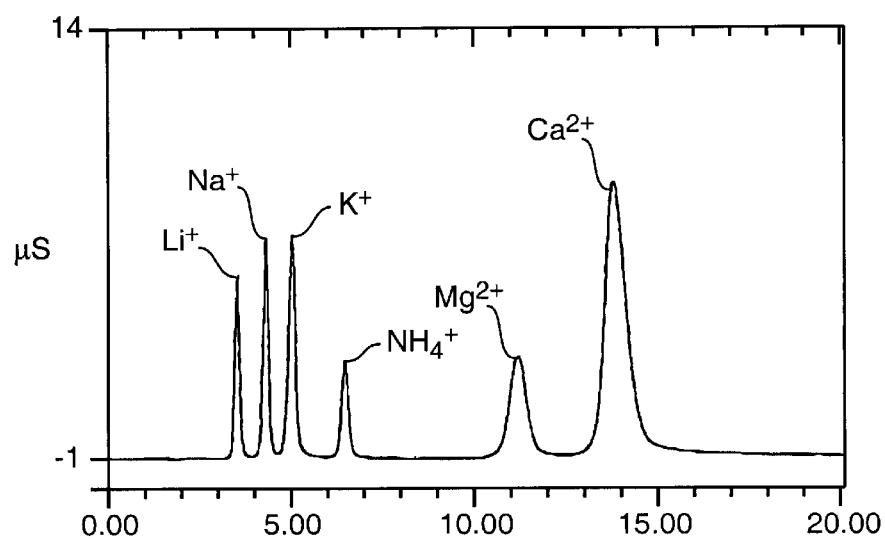
FIG._5

CONTINUOUS ELECTROLYTICALLY REGENERATED PACKED BED SUPPRESSOR FOR ION CHROMATOGRAPHY

BACKGROUND OF THE INVENTION

The present invention relates to method and apparatus using continuous suppression of electrolyte in eluents particularly for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,926,559.

Suppression or stripping of the electrolyte is described in the above prior art references by a bed of ion exchange resin particles commonly referred to as a packed bed suppressor (PBS). The PBS requires periodic regeneration by flushing with an acid or base solution.

While packed bed suppressors have proven useful in ion chromatography, there are a number of disadvantages of a PBS. These disadvantages include a) periodic regeneration of the PBS which interrupts sample analysis, b) a loss of resolution due to band broadening in the PBS and c) changes in retention of certain analytes as a function of the degree of exhaustion of the PBS.

The volume and capacity of the PBS is generally large relative the separation column to contain sufficient ion exchange resin so that the suppression reaction can be performed for a large number of analysis (e.g. 15 to 50) prior to regeneration. By making the volume and capacity of the suppressor sufficiently large, the need to regenerate is less frequent which permits a larger number of samples to be analyzed before the system must be disrupted to regenerate the suppressor. Regeneration typically requires placing the suppressor out of line of the analytical system and pumping a concentrated acid or base solution (regenerant) through the suppressor.

If the suppressor's void volume is too large, the separation of the analytes achieved in the separator column is compromised due to re-mixing of the analytes in the void volume, resulting in lower resolution. Thus, the suppressor volume is a compromise between regeneration frequency and chromatographic resolution.

The regeneration process typically requires 20–60 minutes, depending on the volume of the suppressor. A strong acid or base solution is first pumped through the PBS in order to convert the resin to the acid ($H_3O^+$) or base ($OH^-$) form. After this conversion, deionized water is pumped through the suppressor until any traces of the highly conductive acid or base regenerant have been removed. The PBS is then placed back in line with the analytical system and is allowed to equilibrate before sample analysis is performed.

In U.S. Pat. Nos. 5,597,734 and 5,567,307, a method is described of regenerating a packed bed suppressor after each analysis. In this apparatus, the packed bed suppressor has limited capacity for just one or several sample analysis before the suppressor requires regeneration. The liquid flow through the low volume packed bed suppressor is used with suitable valving to pass liquid stream through the system. During analysis, eluent from the separator passes through the suppressor and to the conductivity cell. Immediately after the analysis, valving diverts a flow of chemical regenerant through the suppressor for regeneration. The valving then diverts eluent to the suppressor for equilibration prior to sample analysis. The regeneration and equilibration of this type of PBS can be performed in a short time with a small volume PBS.

Another form of packed bed suppression uses intermittent electrolytic regeneration as described and published in U.S. Pat. No. 5,633,171. A commercial product using this form of suppression is described in "Electrochemically regenerated solid-phase suppressor for ion chromatography" Saari-Nordhaus, R. and Anderson, J. M., American Laboratory, February 1996. In this product, an electrical potential is applied through the resin in the packed bed suppressor while flowing an aqueous liquid stream to electrolyze water in the stream. For the analysis of anions, a PBS containing fully sulfonated cation exchange is fitted with a cathode embedded in the resin at the suppressor inlet and an anode embedded in the resin at the suppressor outlet. Hydronium ions generated at the anode displace the sodium ions which associate with the hydroxide ions for passage to waste, in this instance through the conductivity cell. This process electrochemically regenerates the suppressor, and after the electrical potential is turned off, the device can be used as a conventional PBS. In a further embodiment, a second ion exchange resin bed is used with suitable valving to pass liquid streams through the system. In one alternative of this system, a second sample in an eluent stream is chromatographically separated, typically on a chromatographic column using an eluent. The eluent and separated second sample flow through a second packed bed suppressor including ion exchange resin to convert the electrolyte to weakly ionized form. Then, the separated sample ionic species in the suppressor effluent are detected in the detector. The effluent then flows through the first packed bed suppressor, forming the aqueous liquid stream required for regeneration and an electrical potential is applied and regeneration of the first packed bed suppressor is accomplished. The second suppressor may be similarly regenerated by positioning it after the detection cell and flowing through the detector effluent of the first sample and applying an electrical potential. This form of suppression does not require an external regenerant source and allows for uninterrupted operation although it is not considered continuous. This system uses two PBS's, additional valving and electronics to control the valve switching and timing.

A different form of a suppressor is described and published in U.S. Pat No. 4,474,664, in which a charged ion exchange membrane in the form of a fiber or sheet is used in place of the resin bed. The sample and eluent are passed on one side of the membrane with a flowing regenerant on the other side, the membrane partitioning the regenerant from the effluent of the chromatographic separation. The membrane passes ions of the same charge as the exchangeable ions of the membrane to convert the electrolyte of the eluent to weakly ionized form, followed by detection of the ions.

Another suppression system is disclosed in U.S. Pat. No. 4,459,357. There, the effluent from a chromatographic column is passed through an open flow channel defined by flat membranes on both sides of the channel. On the opposite sides of both membranes are open channels through which regenerant solution is passed. As with the fiber suppressor, the flat membranes pass ions of the same charge as the exchangeable ions of the membrane. An electric field is passed between electrodes on opposite sides of the effluent channel to increase the mobility of the ion exchange. One problem with this electrodialytic membrane suppressor system is that high voltages (50–500 volts DC) are used. As the liquid stream becomes deionized, electrical resistance increases, resulting in substantial heat production. Such heat can be detrimental to effective detection because it increases noise and decreases sensitivity.

In U.S. Pat. No. 4,403,039, another form of electrodialytic suppressor is disclosed in which the ion exchange membranes are in the form of concentric tubes. One of the electrodes is at the center of the innermost tube. One problem with this form of suppressor is limited exchange capacity. Although the electrical field enhances ion mobility, the device is still dependent on diffusion of ions in the bulk solution to the membrane.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant The patent also discloses the possibility of using water to replace the regenerant solution in the electrodialytic mode.

Another improvement in suppression is described in U.S. Pat. No. 5,248,426. This form of suppressor was introduced in 1992 by Dionex Corporation under the name "Self Regenerating Suppressor" (SRS). A direct current power controller generates an electric field across two platinum electrodes to electrolyze water in the regenerant channels. Functionalized ion-exchange screens are present in the regenerant chambers to facilitate electric current passage with permselective ion-exchange membrane defining the chromatography eluent chamber, as in the '098 patent. After detection, the chromatography effluent is recycled through the suppressor to form a flowing sump for electrolyte ion as well as providing the water for the electrolysis generating acid or base for suppression. Thus, no external regenerant is required and the suppressor is continuously regenerated.

In copending application, Ser. No. 08/925,813, filed Sep. 4, 1997, now abandoned entitled Ion Chromatographic Method and Apparatus Using a Combined Suppressor and Eluent Generator, incorporated herein by reference ("the copending application"), method and apparatus are provided for generating an acid or base eluent in an aqueous solution and for simultaneously suppressing conductivity of the eluent in an ion exchange bed after chromatographic separation in an ion chromatography system. Referring first to the apparatus, the suppressor and eluent generator comprises: a flow-through suppressor and eluent generator bed of ion exchange resin having exchangeable ions of one charge, positive or negative, having an inlet and an outlet section in fluid communication with fluid inlet and outlet conduits, respectively; an electrode chamber disposed adjacent to said suppressor and eluent generator bed inlet section and having fluid inlet and outlet ports; a flowing aqueous liquid source in fluid communication with said electrode chamber inlet port; a first electrode disposed in said electrode chamber; a barrier separating said suppressor and eluent generator bed from said electrode chamber, the barrier preventing significant liquid flow but permitting transport of ions only of the same charge as said suppressor and eluent generator bed resin exchangeable ions; and a second electrode in electrical communication with said resin bed outlet section.

In one embodiment of the copending application ion chromatography apparatus, the generator is used with a flow-through separator bed of ion exchange resin having exchangeable ions of opposite charge to the exchangeable ions of said suppressor and eluent generator bed, said separator bed having a sample inlet port and an effluent outlet port, said electrode chamber outlet port being in fluid communication with said separator bed inlet port, said separator bed outlet being in fluid communication with said suppressor and eluent generator bed inlet port, and a detector downstream from the generator. The aqueous liquid source can be an independent reservoir or can be a recycle conduit from the detector.

For anion analysis, one method includes (a) flowing an aqueous liquid sample stream containing anions to be detected and cation hydroxide through a separator bed of anion exchange resin with exchangeable anions to form liquid effluent including separated anions and said cation hydroxide; (b) flowing said aqueous effluent from said separator bed through a flow-through suppressor and eluent generator bed comprising cation exchange resin including exchangeable hydronium ions, so that said cation hydroxide is converted to weakly ionized form, and some of said exchangeable hydronium ions are displaced by cations from said cation hydroxide, said suppressor and eluent generator bed having inlet and outlet sections and inlet and outlet ports, liquid effluent from said suppressor and eluent generator bed flowing through said outlet port; (c) flowing an aqueous liquid through a cathode chamber proximate to said suppressor and eluent generator bed inlet section and separated by a barrier therefrom, said barrier substantially preventing liquid flow between said cathode chamber and said suppressor and eluent generator bed inlet section while providing a cation transport bridge therebetween; (d) applying an electrical potential between a cathode in said cathode chamber and an anode in electrical communication with said suppressor and eluent generator bed outlet section, whereby water is electrolyzed at said anode to generate hydronium ions to cause cations on said cation exchange resin to electromigrate toward said barrier and to be transported across said barrier toward said cathode in said cathode chamber while water in said chamber is electrolyzed to generate hydroxide ions which combine with said transported cations to form cation hydroxide in said cathode chamber; (e) flowing said cation hydroxide from said cathode chamber to the inlet of said separator column; and (f)

flowing the effluent liquid from said suppressor and eluent generator bed past a detector in which said separated anions are detected.

After passing the detector in step (f), the effluent liquid can be recycled to said cathode chamber. The system can be used for cation analysis by appropriate reversal of the cation and anion functional components.

In a second embodiment of the copending application suppressor and eluent generator bed, the second electrode is not in direct contact with the suppressor and eluent generator bed. Instead, it is adjacent the suppressor and eluent generator bed outlet section in a second electrode chamber similar to the one described above. In this embodiment, aqueous liquid exiting the detector may be recycled to the inlet of the second electrode chamber.

In a third embodiment, similar to the second one, aqueous liquid from a reservoir is pumped to the inlet of the second electrode chamber. Liquid from the outlet of the second electrode chamber is directed to the inlet of the first electrode chamber. Liquid flowing out of the first electrode chamber is directed to the inlet of the separator bed.

The copending application also discloses a method of anion analysis using two electrode chambers separated from the suppressor and eluent generator bed which includes the following steps: (a) flowing an aqueous liquid sample stream containing anions to be detected and a cation hydroxide through a separator bed of anion exchange resin with exchangeable anions to form a liquid effluent including separated anions and said cation hydroxide; (b) flowing said aqueous liquid effluent from said separator bed through a flow-through suppressor and eluent generator bed comprising cation exchange resin including exchangeable hydronium ions, so that said cation hydroxide is converted to weakly ionized form, and some of said exchangeable hydronium ions are displaced by cations from said cation hydroxide, said suppressor and eluent generator bed having inlet and outlet sections and inlet and outlet ports, liquid effluent from said suppressor and eluent generator bed flowing through said outlet port; (c) flowing an aqueous liquid through an anode chamber proximate to said suppressor and eluent generator bed outlet section and separated by a first barrier therefrom, said first barrier substantially preventing liquid flow between said anode chamber and said suppressor and eluent generator bed outlet section while providing a cation transport bridge therebetween, said aqueous liquid exiting said anode chamber as an anode chamber aqueous liquid effluent; (d) flowing an aqueous liquid through a cathode chamber proximate to said suppressor and eluent generator bed inlet section and separated by a second barrier therefrom, said second barrier substantially preventing liquid flow between said cathode chamber and said suppressor and eluent generator bed inlet section while providing a cation transport bridge therebetween; (e) applying an electrical potential between an anode in said anode chamber and a cathode in said cathode chamber, whereby water is electrolyzed at said anode to generate hydronium ions which are transported across said first barrier to cause cations on said cation exchange resin to electromigrate toward said second barrier and to be transported across said second barrier toward said cathode in said cathode chamber while water in said cathode chamber is electrolyzed to generate hydroxide ions which combine with said transported cations to form cation hydroxide in said cathode chamber; (f) flowing said cation hydroxide from said cathode chamber to the inlet of said separator bed; and (g) flowing the effluent from said suppressor and eluent generator bed past a detector in which said separated anions are detected.

The anode chamber aqueous liquid effluent may be recycled through said cathode chamber. Alternatively, after detection in step (g), the suppressor and eluent generator bed effluent may be recycled through said anode chamber.

The history of ion chromatography suppression as of 1993 was summarized in Rabin, S. et al. *J. of Chromatog.* 640 (1993) 97–109, incorporated herein by reference.

SUMMARY OF THE INVENTION

In the present invention, method and apparatus are provided for continuously electrolytically suppressing the conductivity of an eluent in an ion exchange bed previously used in separating ions in a separator bed.

Referring first to the apparatus, the suppressor includes (a) a flow-through suppressor bed of ion exchange resin having exchangeable ions of one charge, positive or negative, having a liquid sample inlet and an outlet section in fluid communication with suppressor inlet and outlet ports, respectively, (b) a first electrode chamber disposed adjacent to said suppressor inlet section and having fluid inlet and outlet ports, (c) a first electrode disposed in said first electrode chamber, (d) a barrier separating said suppressor bed from said first electrode chamber, said barrier preventing significant liquid flow but permitting transport of ions only of the same charge as said suppressor bed resin exchangeable ions, (e) a second electrode in electrical communication with said resin bed outlet section, and (f) a recycle conduit providing fluid communication between said suppressor outlet port and said electrode chamber inlet port.

Opposite faces of the barrier are in electrical communication with the first and second electrodes, respectively, in direct contact or through conductive medium. For example, the second electrode is in electrical communication with the barrier through the conductive suppressor bed.

The suppressor is normally used in combination with (g) a flow-through separator bed of ion exchange resin having exchangeable ions of opposite charge to the exchangeable ions of said suppressor bed, said separator bed having a sample inlet port and an outlet port, said separator bed outlet port being in fluid communication with said suppressor bed inlet port, and with a detector disposed in the path of said recycle conduit to detect sample flowing through said conduit.

In one embodiment, the second electrode is disposed in contact with said ion exchange resin in said suppressor outlet section. In another embodiment, the suppressor combination includes (h) a second electrode chamber disposed adjacent to said suppressor outlet section and having fluid inlet and outlet ports, and (i) a second barrier separating said suppressor bed from said second electrode chamber, said barrier preventing significant liquid flow but permitting transport of ions only of the same charge as said suppressor bed resin exchangeable ions, said second electrode being disposed in said second electrode chamber.

For anion analysis, the suppressor bed ion exchange resin is a cation exchange resin, the first electrode is a cathode, and the second electrode is an anode. The opposite polarities apply for cation analysis.

Referring to one embodiment of the method, anion analysis is performed by the following steps: (a) flowing an aqueous liquid sample stream containing anions to be detected and cation hydroxide through a separator bed of anion exchange resin with exchangeable anions to form liquid effluent including separated sample anions and said cation hydroxide,(b)flowing said aqueous effluent from said separator bed through a flow-through suppressor and comprising cation exchange resin including exchangeable hydronium ions, so that said cation hydroxide is converted to weakly ionized form, and some of said exchangeable hydronium ions are displaced by cations from said cation hydroxide, said suppressor bed having inlet and outlet sections and inlet and outlet ports, liquid effluent from said suppressor bed flowing through said outlet port, (c) flowing the effluent liquid from said suppressor past a detector in which said separated sample anions are detected, (d) recycling said liquid effluent from said detector through a cathode chamber proximate to said suppressor bed inlet section and separated by a first barrier therefrom, said first barrier substantially preventing liquid flow between said cathode chamber and said suppressor bed inlet section while providing a cation transport bridge therebetween, and (e) applying an electrical potential between a cathode in said cathode chamber and an anode in electrical communication with said suppressor bed outlet section, whereby water is electrolyzed at said anode to generate hydronium ions to cause cations on said cation exchange resin to electromigrate toward said barrier and to be transported across said barrier toward said cathode in said cathode chamber while water in said cathode chamber is electrolyzed to generate hydroxide ions which combine with said transported cations to form cation hydroxide in said cathode chamber.

In another embodiment, the liquid effluent is recycled through an anode chamber proximate to said suppressor bed outlet section and separated by a barrier of the same type as the first barrier. The anode is disposed in the anode chamber.

Cation analysis is performed by the same methods with a corresponding reversal of polarity and resin and barriers of opposite charge.

BRIEF DESCRIPTION OF THE DRAWINGS

FIG. 1 is a schematic view of one system according to the present invention using a continuous electrolytically regenerated (CER) packed bed suppressor.

FIG. 2 is a schematic view of a two electrode chamber CER packed bed suppressor according to the invention.

FIGS. 3–5 are chromatograms illustrating use of the present invention.

DETAILED DESCRIPTION OF PREFERRED EMBODIMENTS

In general, the present invention relates to ion chromatography using continuous electrochemical regeneration of a packed bed suppressor. Method and apparatus are provided using electrolytic regeneration of a packed bed suppressor containing ion exchange resin. Ion chromatography is performed in a conventional manner by chromatographic separation, chemical suppression in a packed bed, and detection. The packed bed suppressor has electrodes in electrical contact with the resin, which permits continuous electrochemical regeneration. The electrodes are separated from the resin by a barrier which permits ion movement but is impermeable to liquid flow under typical operating pressures. The device may have several ion exchange connectors and electrodes in order to increase the flux of regenerant ions and eluent counter-ions. Electrochemical regeneration of the packed bed suppressor, by application of a direct current (DC) voltage, is continuous during the analysis by electrolytically splitting an aqueous liquid stream which is separated from the eluent flow by the ion exchange connectors. The electrolytically generated hydronium or hydroxide passes through the ion exchange connector and migrates through the ion exchange resin to neutralize the eluent. Eluent counter-ions pass through the ion exchange connector and are swept to waste by the aqueous liquid stream. In one embodiment, the aqueous liquid stream is the suppressed eluent. In another embodiment, the aqueous liquid stream is an independent water source, preferably deionized water.

The gases created by the electrolysis of the aqueous liquid stream, hydrogen and oxygen, are separated from the eluent flow by the ion exchange connector so that detection is not adversely affected by the gas production.

Apparatus is provided to perform the above continuously regenerated packed bed suppressor methods. Such apparatus includes a suppressor with an ion exchange resin bed, liquid barriers that prevent liquid flow but permit ion transport and means for applying a continuous electrical potential to electrolyze water in a flowing stream and thus continuously regenerate suppressor ion exchange resin to suppress the electrolyte in the eluent stream.

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The purpose of the suppressor stage is to reduce the conductivity, and hence noise, of the analysis stream background while enhancing the conductivity of the analytes (i.e., increasing the signal/noise ratio), while maintaining chromatographic efficiency.

In a preferred embodiment, the present invention relates to the use of a continuous electric field during electrochemical suppression to minimize noise during detection of the ionic species. Specifically, it has been found that the suppressor can be continuously regenerated to convert the chromatography electrolyte to a weakly dissociated form in an uninterrupted manner. When used in this configuration, the requirement for chemical regenerant is eliminated. Also, the device can tolerate high system backpressure. Further, it has low noise since the electrolysis reaction occur in a chamber separate from the eluent flow and reduced manufacturing costs due to the simple design. As used herein, the term continuous electrolytically regenerated packed bed suppressor (CERPBS) will refer to this type of system.

In the CERPBS, the electrodes must be in electrical contact with the ion exchange resin either through an ion exchange connector in contact with the resin or the electrode is directly embedded in the resin. At least one of the electrodes is separated from the eluent flow path by the ion exchange connector, but still in electrical contact or communication with the resin. Also, the barrier is in electrical communication with both the suppressor bed resin and both electrodes. This configuration permits eluent counter-ions to be removed from the eluent stream and replaced with either hydroxide or hydronium to form water or other weakly conducting aqueous streams. For anion analysis using sodium hydroxide eluent, the suppressor contains cation exchange resin which is continually regenerated to the hydronium ion form by formation of hydronium ions at the anode, which migrate toward the cathode, displacing sodium ions from the ion exchange sites. At least the cathode is separated from the eluent stream by the ion exchange connector so that the sodium ions are removed from the eluent stream and exit the suppressor as sodium hydroxide.

Current is maintained between the electrodes by movement of ions along ion exchange sites in the ion exchange material in the bed. It is also possible to have the anode separated from the eluent by an ion exchange connector. In this configuration, the electrolytically produced hydronium ion passes through the ion exchange connector and into the cation resin being driven towards the cathode under the force of the electric field. This configuration permits the continuous regeneration of the suppressor without the need to interrupt the analysis cycle to regenerate the suppressor.

Referring to FIG. 1, an ion chromatography system is illustrated using a CERPBS. The system includes analytical pump 10 connected by tubing 12 to sample injection valve 14 which in turn is connected by tubing 16 to a flow-through chromatographic separator 18 typically in the form of a chromatographic column packed with chromatographic resin particles. The effluent from chromatographic column 18 flows through tubing 20 to a packed ion exchange resin bed flow-through suppressor 22. Typically, suppressor 22 is formed of a column 24 packed with an ion exchange resin bed 26 of the type used for ion chromatography suppression. Electrodes, in a form to be described below, are spaced apart in the suppressor, with at least one electrode separated from the resin by a barrier described below. The electrodes are connected to a direct current power supply 27 by leads 27a and 27b. The configuration is such that with an aqueous stream flowing through the suppressor and the application of power, water in the aqueous stream is electrolyzed to form a source of hydronium ion or hydroxide ion to continuously regenerate the ion exchange resin bed during the analysis.

The suppressor effluent is directed through tubing 30 to a suitable detector and then eventually to waste. A preferred detector is a conductivity detector 32 with a flow-through conductivity cell 34. The chromatography effluent flows through cell 34.

Suppressor 22 generates hydronium ions (and oxygen gas) at the anode and hydroxide ions (and hydrogen gas) at the cathode. If the power supply 26 were turned off, the system would operate in the manner of a standard ion chromatography system with a packed bed suppressor. That is, a water-containing eluent solution including electrolyte is directed from pump 10 and through tubing 12. Sample is injected through sample injection valve 14, and is directed by tubing 16 into chromatographic column 18 to form a first chromatography effluent including separated ionic species of the sample. For simplicity of description, unless otherwise specified the system will be described with respect to the analysis of anions using an eluent solution including sodium hydroxide as the electrolyte.

A preferred form of resin is a bed packed with resin particles. However, other forms of resin beds can be used, such as disclosed in the copending application, incorporated by reference. Suppressor 22 serves to suppress the conductivity of the electrolyte in the eluent supplied to separator 18 from pump 10 but not the conductivity of the separated anions. The conductivity of the separated anions is usually enhanced in the suppression process.

A suitable sample is supplied through sample injection valve 14 which is carried in a solution of eluent supplied from pump 10. Anode 36 is disposed at the outlet end of resin bed 26 in intimate contact with the resin therein. The effluent from bed 26 exits through port 37 and is directed to a detector suitably in the form of a flow-through conductivity cell 34, for detecting the resolved anions in the effluent, connected to a conductivity meter 32.

In the detector, the presence of anions produces an electrical signal proportional to the amount of ionic material. Such signal is typically directed from the cell 34 to a conductivity meter 32, thus permitting the detection of separated ionic species of interest (anions for anion analysis).

In a preferred embodiment, detection is by electrical conductivity and so the present system is described using ion conductivity detector. However, other forms of detectors may be used including absorbance, mass spectrometry, and inductive coupled plasma. Detection of the present invention will be described with respect to a conductivity detector.

The system also includes means for pressurizing the effluent from suppressor 22 prior to detection to minimize adverse effect of gases (hydrogen or oxygen) generated in the system as will be described hereinafter. As illustrated in FIG. 1, such pressurizing means comprises a flow restrictor 38 downstream of conductivity cell 34 to maintain the ion chromatography system under pressure.

Column 24 is typically formed of plastic conventionally used for an ion exchange column. It has a cylindrical cavity of a suitable length, e.g., 60 mm long and 4 mm in diameter. It is packed with a high capacity cation exchange resin, e.g., of the sulfonated polystyrene type. The resin is suitably contained in the column by a porous frit which serves to provide an outlet to the column. In the illustrated embodiment, the porous frit is porous electrode 36 which serves the dual function of containment of the resin and as an electrode.

Forms of ion exchange beds other than packed resin beds can be used in column 24, such as a porous continuous structure with sufficient porosity to permit flow of an aqueous stream at a sufficient rate for use in chromatography without undue pressure drop and with sufficient ion exchange capacity to form a conducting bridge of cations or anions between the electrodes. One form of structure is a porous matrix or a sponge-like material formed of sulfonated, cross-linked polystyrene with a porosity of about 10 to 15% permitting a flow rate of about 0.1 to 3 ml/min. without excessive pressure drop.

A barrier 40 separates bed 26 from electrode 42 in the interior of a hollow housing defining electrode chamber 44 preventing any significant liquid flow but permitting transport of ions only of the same charge as the charge of exchangeable ions on resin bed 26. For anion analysis, barrier 40 is suitably in the form of a cation exchange membrane or plug separating electrode chamber 44 from the cation exchange resin.

Electrode 42 in electrode chamber 44 also suitably is in the form of an inert metal (e.g., platinum) porous electrode in intimate contact with barrier 40. An electrode is fabricated in a way to permit good irrigation of the electrode/membrane interface when water is passed through electrode chamber 44. The electrode is suitably prepared by crumpling and forming a length of fine platinum wire so as to produce a roughly disc-shaped object that allows easy liquid flow throughout its structure and at the electrode membrane interface. Good contact between the disc-electrode 42 and barrier 40 is maintained simply by arranging that the one press against the other. The electrode can extend across all or part of the aqueous liquid flow path through electrode chamber 42 to provided intimate contact with the flowing aqueous stream.

A conduit 48 is provided to direct the aqueous liquid stream to the inlet 50 of electrode chamber 44. Conduit 52 takes the effluent from chamber 44 to waste. All conduits may be made from narrow bore plastic tubing. However, if desired, conduit 50, 52 and 54 may be made out of stainless steel tubing. When these metal conduits are allowed to touch the platinum electrodes, they make electrical contact with the electrodes as well as being conduits for fluid flow. This provides a means of making electrical contact with the electrodes that is at the same time easy to seal against liquid leakage.

The line X—X is illustrated across the resin bed 26. For reasons which will be explained below, the resin above the dotted line is predominantly or substantially completely in the form of the cation counter ion of the base used as the electrolyte during separation. Below the line X—X, the resin is predominantly or completely in the hydronium form. The line X—X represents the interface. As used herein, the terms "anion or cation or ion exchange beds" refer to flow-through beds of anion or cation exchange material through which the aqueous liquid stream flows. Unless otherwise stated, the term "cation" excludes hydronium ions and the term "anion" excludes hydroxide ions. Because of its ready availability and known characteristics, a preferred form of ion exchange bed is a packed ion exchange bed of resin particles. It is desirable that the resin particles be tightly packed in the bed, to form a continuous ion bridge or pathway for the flow of ions between electrodes 36 and 42. Also, there must be sufficient spacing for the aqueous stream to flow through the bed without undue pressure drops.

As defined herein, the portion of bed 26 above the line X—X is referred to as the suppressor bed inlet section 26a. Conversely, the portion of the bed below the line X—X is referred to as the suppressor bed outlet section 26b. As illustrated, barrier 40 of electrode chamber 44 is disposed adjacent bed inlet section 26a and, therefore, primarily is in the cation form.

The principle of operation of the system for anion analysis is as follows. An aqueous liquid stream containing anions to be detected and a cation (e.g., potassium) hydroxide flows through separator bed 18 of anion exchange resin with exchangeable anions to form a liquid effluent including separated anions and the cation hydroxide. Anion exchange resin in bed 18 is of a suitable conventional low capacity form used for ion chromatography as illustrated in U.S. Pat. Nos. 3,897,213, 3,920,397, 3,925,019 and 3,926,559. For example, bed 18 has typically a total capacity of about 0.01 to 0.1 milliequivalents. As is conventional, the anion exchange capacity of the separator is low in comparison to that of the suppressor.

The ratio of the capacities of the ion exchange resin in suppressor bed 26 to separator bed 18 may be the same as used for ion chromatography using a conventional packed bed suppressor, e.g. from 10:1 to 1000:1.

For anion analysis, a polarizing DC potential is applied between cathode 42 and anode 36, and the following reactions take place.

The water is electrolyzed and hydronium ions are generated at anode 36 according to the following reaction:

$$H_2O - 2e \rightarrow 2H^+ + \tfrac{1}{2}O_2 \rightarrow. \tag{1}$$

This causes cations in the cation exchange resin bed 26 to migrate to barrier 40. This, in turn, displaces hydronium ions upwardly through bed 26 which causes a similar displacement of cations ahead of them. The cations electromigrate toward the barrier 40 to be transported across the barrier 40 toward cathode 42 in cathode chamber 44 while water is electrolyzed at cathode 42 to generate hydroxide ions according to the following reaction:

$$2\,H_2O + 2e \rightarrow 2OH^- + H_2 \rightarrow. \tag{2}$$

The cations which have transported across the barrier combine with the generated hydroxide ions to form cation hydroxide in cathode chamber 44. The effluent from separator bed 60 exits through outlet port 37 and conduit 30 and percolates through the cation form resin in inlet bed section 26 until it reaches the hydronium form resin in bed section 26 where it is neutralized while the cation is retained on the resin. At this point, the anion salts are converted to their respective acids and the cation hydroxide is converted to weakly ionized form, water.

The suppressed effluent liquid containing the separated anions leaves bed 26 through port 27 and conduit 30 and passes to conductivity cell 34 in which the conductivity of the separated anions is detected.

The effluent from conductivity cell 34 passes through flow restrictor 38 and conduit 48 and is recycled to electrode chamber 44. This provides a source of aqueous liquid to permit continuous reaction in electrode chamber 44 by passing the formed acid or base to waste in a continuous stream.

The net result of the electrode reactions and the electromigration of the resin counterions are: the production of cation (e.g., potassium) hydroxide in the region of the cathode, and electrolytic gases at the two electrodes. Specifically, the electrode reactions produce, hydrogen and oxygen which are carried out of the suppressor into the chromatography system.

When the hydronium ion/cation boundary line X-X is reached, the cation (shown as potassium) hydroxide is neutralized as a conventional suppression according to the following equation:

$$KOH + H^+R^- \rightarrow K^+R^- + H_2O, \tag{3}$$

wherein R is the cation exchange resin. The $K^+R^-$ indicates that the ion exchange resin retains the cation as its exchangeable ion.

The flux of hydronium "upwards" in the resin phase toward bed inlet section 26a is equivalent to or greater than the flux of cation hydroxide "downwards" in the mobile phase toward bed outlet section 26b. Since the balance prevails at different current levels, the position of the hydronium/cation boundary line X—X remains fixed. Thus, the system operates as a continuous suppressor of cation hydroxide.

The system of FIG. 1 has been described with respect to a system for the analysis of anions. However, the system is also applicable to the analysis of cations. In this instance, electrode 36 is a cathode and electrode 42 is an anode. The polarity type resin is reversed. Thus, the resin in separator bed 18 is a cation exchange resin and the resin in suppressor bed 26 is an anion exchange resin. The plug or membrane 40 is an ion exchanging material.

Briefly described, the system works as follows for the cation analysis. The aqueous liquid stream containing cations to be detected and an acid electrolyte aqueous eluent are directed through separator bed 18 including cation exchange resin. The effluent from separator bed 18 flows through suppressor bed 26 including anion exchange resin with exchangeable hydroxide ions. The acid in the eluent is converted to weakly ionized form. Some of the exchangeable hydroxide is displaced by anions from the acid.

An electrical potential is applied between the cathode 36 and anode 42. Water is electrolyzed at electrode 36 to generate hydroxide to cause anions on the anion exchange resin bed to electromigrate toward barrier 40 to be transported across the barrier toward the positively charged anode 42 in the electrode chamber 44 while water in chamber 44 is electrolyzed to generate hydronium ions which combine with the transported anions to form acid in the electrode chamber 44. The effluent liquid from the suppressor bed 26 flows past detector 32 in which separated cations are detected and is recycled to electrode chamber 44.

The exchangeable cations or anions for suppressor bed 26 and, thus for the acid or base electrolyte in the aqueous eluent, must also be sufficiently water soluble in base or acid form to be used at the desired concentrations. Suitable cations are metals, preferably alkali metals such as sodium, potassium, lithium and cesium. Known packing for high capacity ion exchange resin beds are suitable for this purpose. Typically, the resin support particles may be in the potassium or sodium form. Potassium is a particularly effective exchangeable cation because of its high conductance. Suitable other cations are tetramethyl ammonium and tetraethyl ammonium. Analogously, suitable exchangeable anions for cation analysis include chloride, sulfate and methane sulfonate. Typically, resin support particles for these exchangeable anions include Dowex 1 and Dowex 2.

Another embodiment of the invention is illustrated in FIG. 2. Like the embodiment in FIG. 1, the FIG. 2 embodiment may be used with a conventional packed ion exchange resin bed separator column. The principal difference between the embodiments of FIGS. 1 and 2 is that in the latter one, there are two external electrode chambers rather than one so that the analyte ions are prevented from contacting any electrodes.

FIG. 2 schematically illustrates only that portion of the system downstream from the separation column. In the illustrated system the effluent from the separator column flows in conduit 60 through suppressor 62 which includes a housing (suitably of cylindrical cross-section) including a body 64 defining a central bore, screw threaded top and bottom caps 66 and 68, and top and bottom flow-through bed supports 70 and 72, respectively, at opposite ends of the bore. Suppressor 62 contains a high-capacity ion exchange resin bed 68 of the type described above. Electrode chamber 70 contains electrode 72 separated from bed 68 by barrier 74, all of the same type described above. The difference from FIG. 1 is that FIG. 2 includes an electrode chamber 76 containing a second electrode 78 separated by barrier 80 from bed 68. Both electrode chambers 70 and 76 may be of the same type with the exception that the electrodes are of opposite polarity. Electrode 78 in electrode chamber 76 replaces electrode 36 in FIG. 1 which was in direct contact with the resin bed of the suppressor. The electrodes are connected to a DC power supply, not shown, and are suitably formed of platinum. Beds supports 70 and 72 are first positioned and then caps 66 and 68 are screwed into a secure position. As is conventional, the end caps include screw-threaded ports for connecting to the inlet and outlet tubing.

The effluent from suppressor 62 flows through line 82 and through detector 84 and line 86 to electrode chamber 76. The effluent from electrode chamber 76 is further recycled through line 88 to the inlet side of electrode chamber 70. The effluent from electrode chamber 70 passes through line 90 to waste.

In this embodiment, resin bed 68, electrodes 72 and 78, and barriers 74 and 80 are in electrical communication. However, barriers 74 and 80 separate the sample eluent flow through the suppressor 62 from the liquid flow in the anode and cathode chambers. The same reactions as in FIG. 1 occur at the anode and cathode. Specifically, for anion analysis, the foregoing description applies to the reaction in cathode chamber 70. It is disposed above the line X—X in the inlet portion 68a of bed 68. Similarly, the same reaction occurs at anode 78 as described in FIG. 1 with respect to anode 36. However, the presence of the barrier creates the following difference in operation. The hydronium ions generated at anode 78 electrophoretically pass through barrier 80 to the cation exchange resin in bed 68 where they are driven upwardly in the resin toward cathode 72 in the manner described above. Similarly, cations from the eluent are displaced from the cation exchange resin by the upward flux of hydronium ions which combine with the eluent hydroxide to form water. This reaction scheme is as also set forth above. Similarly, the cations are electrophoretically driven through barrier 74 to electrode 72 where they associate with the hydroxide ions to form a base for passage to waste. The oxygen produced at the anode compartment and the hydroxide produced in the cathode department are swept away with the sodium hydroxide. Thus, no flow restrictor is necessary to minimize the effect of such gases on analysis since the gases are separated from the analytical system.

Another advantage of separating the anode and cathode by barriers 74 and 80 is that the eluent stream flowing through bed 68 does not pass over the electroactive surface of the electrodes where a solvent or analyte could be electrochemically modified. This can be important when an organic modifier is used in the eluent. For example, methanol, a common organic modifier with sodium hydroxide eluents, can be oxidized at the anode to formic acid which raises the background conductivity. With the electrode separated from the eluent compartment by the barriers, the eluent stream is not exposed to undesirable electrochemical reactions.

The proper operating current for the CERPBS depends on the eluent composition. For the anion example, the electrochemically generated hydronium flux must be greater than or equal to the incoming sodium hydroxide flux. This assures that every mole of hydroxide is neutralized by a mole of hydronium and that the sodium is displaced by hydronium through the ion exchange connector, to the cathode compartment which is swept to waste. Typically, the current is 110–160% of the eluent flux.

The operating voltage depends on the device geometry, electrode size, electrode spacing as well as the resin and ion exchange connector conductivity.

The device is designed to minimize the voltage drop and typical operating voltages range from 10 to 100 volts. It is generally desirable to operate the device in the constant current mode since current can be directly related to the eluent concentration, and hence the regenerant flux required.

An important feature of the suppressor is the use of means for applying an electrical potential through the ion exchange connectors and across the ion exchange resin. Any number of configurations may be employed so long as the potential is applied to a significant part of the resin for efficient regeneration and the eluent cations are removed through the ion exchange connector. In that regard, the anode and cathode should be spaced apart with the majority of the ion exchange resin disposed therebetween.

The following examples illustrate different aspects of the present invention.

EXAMPLE 1

This example illustrates the use of an continuous electrolytically regenerated packed bed suppressor of the type illustrated in FIG. 1. This example is given for the suppression of sodium hydroxide which is used as an eluent for anion separations. As shown in FIG. 1, a conventional chromatographic system (Dionex Corp., Sunnyvale, Calif.) was used consisting of a pump 10, with injection valve 14 connected to an ion exchange separator column 18. In this experiment, a Dionex anion separator, IonPac AS11 was used. A continuous electrolytically regenerated packed bed suppressor 22, as described in this disclosure, was used. Suppressor 22 includes central flow channel that is 4×70 mm column. Suppressor 22 was packed with 20 μ fully sulfonated polystyrene/8% divinylbenzene which was packed in the sodium form and then converted to the hydronium form with sulfuric acid. A cation exchange membrane AMI-7000 (217 in FIG. 2) from Membrane International, NJ was used as barrier 40 in electrode chamber 44. A power supply from Hoefer Scientific Instruments (CA), Model PS2500, 27, was used to apply a DC voltage to platinum electrodes, 36 and 42. Anode 36, in porous platinum form, was placed at the outlet of suppressor 22 which also acts as a flow-through bed support to retain the resin. A conductivity detector and cell, 32, 34 was used to monitor the effluent from the suppressor. Backpressure was applied to the cell using 15 cm of 0.076 mm id PEEK tubing as restrictor 170. Data was collected using Dionex AI450 Chromatography software.

EXAMPLE 2

In order to demonstrate the dynamic suppression capacity of the device described in Example 1, a gradient separation of anions was performed. In this example, the maximum eluent concentration is 30 mM NaOH. The chromatogram shown in FIG. 4 was obtained under the following conditions:
Column: IonPac AS11
Flow rate: 1.0 mL/min
Eluent: Gradient from 1 mM NaOH to 30 mM NaOH over 15 minutes
Injection: 25 μL of 2 ppm $F^-$, 3 ppm $Cl^-$ and 15 ppm $NO_3^-$ and 15 ppm $SO_4^{2-}$
Applied voltage: 45V
Current: 65 mA

EXAMPLE 3

This example illustrates the use of an continuous electrolytically regenerated packed bed suppressor of the type illustrated in FIG. 2. This example is given for the suppression of sulfuric acid which is used as an eluent for cation separations. As shown in FIG. 1, a conventional chromatographic system (Dionex Corp., Sunnyvale, Calif.) was used consisting of a gradient pump 10, with injection valve 14 connected to an ion exchange separator column 18. In this experiment, a Dionex cation separator, IonPac CS12A was used. A 25 continuous electrolytically regenerated packed bed suppressor, 62 as shown in FIG. 2 and described in this disclosure was used. The suppressor includes central flow channel that is 4×70 mm column. The suppressor was packed with 20 μ fully aminated vinylbenzylchloride-8%divinylbenzene resin which was packed in the hydroxide form. An anion exchange membrane AMI-7001 (74 and 80 in FIG. 2) from Membrane International, NJ was used in the electrode chambers, 70 and 76. A power supply from Hoefer Scientific Instruments (CA), Model PS2500, 27, was used to apply a DC voltage to platinum electrodes, 72 and 78. A conductivity detector and cell, 84 was used to monitor the effluent from the suppressor. Data was collected using Dionex AI450 Chromatography software. Using the above apparatus and the conditions listed below, the chromatogram in FIG. 5 was obtained. The background conductivity of the suppressed eluent was about 0.4 μS-cm indicating complete suppression of the 18 mN sulfuric acid eluent.

Column: IonPac CS12A
Flow rate: 1.0 mL/min
Eluent: 18 mN $H_2SO_4$
Injection volume: 25 μL of 0.5 ppm $Li^+$, 2 ppm $Na^+$, 2.5 ppm $NH_4^+$, 5 ppm$K^+$, 2.5 ppm $Mg^{2+}$, 5.0 ppm $Ca^{2+}$
Applied voltage: 47V
Current: 60 mA
A chromatogram of the results is illustrated in FIG. 5.

EXAMPLE 4

In this example, a flow-through sponge-like cation exchange bed is formed to act as a suppressor for anion analysis.

Styrene and divinylbenzene are copolymerized in the presence of an appropriate catalyst and a porogen. A porogen is an added material which, when removed after the polymerization is complete, creates a macroporosity in the polymerized structure. This porosity should be such that it provides for a ready flow of liquids through the polymer phase while at the same time providing adequate areas of contact between the polymer and liquid phase. The porogen can be a finely divided solid which can be easily removed by dissolution in acid or base (e.g., calcium carbonate or silica), or it can be a solvent which is rejected by the polymer as it forms and is subsequently displaced by another solvent or water. Suitable liquid porogens include an alcohol, e.g., used in the manner described in *Analytical Chemistry, Vol. 68, No. 2*, pp. 315–321, Jan. 15, 1996.

After the porogen is removed, the polymer is sulfonated by commonly known sulfonating agents such as concentrated sulfuric acid or chlorosulfanic acid.

A suitable shape for the polymer is a cylindrical rod which, after sulfonation and conversion to the suitable metal ion form can be placed in the cylindrical cavity of the suppressor column. Preferably, the ion exchange rod is introduced into the column in a slightly shrunken form so that in its typical use environment it swells to form a tight fit with the wall of the column and the cation exchange membrane(s) that separate the ion exchange rod from the electrode compartment(s).

As a final step, the rod is treated so that the part closest to the outlet is in the hydronium form while the part closest to the inlet is in a metal cation form such as the potassium form. This is accomplished by treating the rod with the appropriate amount of acid, or by electrochemically displacing potassium ions with hydronium ions.

What is claimed is:
1. A suppressor for ion chromatography comprising:
   (a) a flow-through suppressor bed of ion exchange resin having exchangeable ions of one charge, positive or negative, having suppressor bed inlet and outlet sections in fluid communication with suppressor inlet and outlet ports, respectively,
   (b) a first electrode chamber disposed adjacent to said suppressor bed and having fluid inlet and outlet ports,
   (c) a first electrode disposed in said first electrode chamber adjacent to said suppressor bed inlet section but not adjacent to said suppressor bed outlet section,
   (d) a first barrier separating said suppressor bed from said first electrode chamber, said barrier preventing significant liquid flow but permitting transport of ions only of the same charge as said suppressor bed resin exchangeable ions, said first electrode being in electrical communication with said first barrier,
   (e) a second electrode disposed in or adjacent to said suppressor bed outlet section in electrical communica- tion therewith but not in or adjacent to said suppressor bed inlet section, and (f) a recycle conduit providing fluid communication between said suppressor outlet port and said first electrode chamber inlet port.

2. The suppressor of claim 1 in combination with:

(g) a flow-through separator bed of ion exchange resin having exchangeable ions of opposite charge to the exchangeable ions of said suppressor bed, said separator bed having a sample inlet port and an outlet port, said separator bed outlet port being in fluid communication with said suppressor bed inlet port.

3. The suppressor combination of claim 2 further comprising a detector disposed in the path of said recycle conduit to detect sample flowing through said conduit.

4. The suppressor combination of claim 2 in which said second electrode is disposed in contact with said ion exchange resin in said suppressor bed outlet section.

5. The suppressor combination of claim 2 further comprising:

(h) a second electrode chamber disposed adjacent to said suppressor bed and having fluid inlet and outlet ports, and (i) a second barrier separating said suppressor bed from said second electrode chamber, said barrier preventing significant liquid flow but permitting transport of ions only of the same charge as said suppressor bed resin exchangeable ions, said second electrode being disposed in said second electrode chamber adjacent to said suppressor bed outlet section.

6. The suppressor combination of claim 5 in which said second barrier is adjacent to said suppressor bed outlet section but not adjacent to said suppressor bed inlet section.

7. The suppressor combination of claim 5 in which said recycle conduit also provides fluid communication with said second electrode chamber inlet port so that fluid in said recycle conduit flows sequentially from said suppressor outlet port through said second electrode chamber and then to said first electrode chamber.

8. The suppressor of claim 1 in which said suppressor bed ion exchange resin is a cation exchange resin, said first electrode is a cathode, and said second electrode is an anode.

9. The suppressor of claim 1 in which said suppressor bed ion exchange resin is an anion exchange resin, said first electrode is an anode, and said second electrode is a cathode.

10. The suppressor of claim 1 in which said first barrier is adjacent to said suppressor bed inlet section but not adjacent to said suppressor bed outlet section.

* * * * *